United States Patent [19]
Wang

[11] Patent Number: 6,041,248
[45] Date of Patent: Mar. 21, 2000

[54] METHOD AND APPARATUS FOR FREQUENCY ENCODED ULTRASOUND-MODULATED OPTICAL TOMOGRAPHY OF DENSE TURBID MEDIA

[75] Inventor: Lihong Wang, College Station, Tex.

[73] Assignee: The Texas A&M University System, College Station, Tex.

[21] Appl. No.: 08/955,671

[22] Filed: Oct. 22, 1997

Related U.S. Application Data

[60] Provisional application No. 60/045,918, May 7, 1997.

[51] Int. Cl.[7] ........................................ A61B 5/00
[52] U.S. Cl. ............................................. 600/407
[58] Field of Search ................ 73/957, 597; 367/7; 356/340; 600/437, 443, 438

[56] References Cited

U.S. PATENT DOCUMENTS

| | | | |
|---|---|---|---|
| 5,033,304 | 7/1991 | Rosen | 73/957 |
| 5,212,667 | 5/1993 | Tomlinson, Jr. et al. | 367/7 |
| 5,293,873 | 3/1994 | Fang | 128/664 |
| 5,528,365 | 6/1996 | Gonatas | 356/340 |

FOREIGN PATENT DOCUMENTS

| | | | |
|---|---|---|---|
| 4419900 | 12/1995 | Germany | G03B 42/00 |

OTHER PUBLICATIONS

Fay A. Marks, et al., "A Comprehensive Approach to Breast Cancer Detection Using Light: Photon Localization by Ultrasound Modulation and Tissue Characterization by Spectral Discrimination", SPIE, vol. 1888, 1993, pp. 500–510.

PCT Search Report dated Sep. 1, 1998.

Lihong Wang, et al., "Ultrasound–Modulated Optical Tomography of Dense Turbid Media", *SPIE*, vol. 2776, pp. 91–102.

Lihong Wang, et al., "Continuous–Wave Ultrasonic Modulation of Scattered Laser Light to Image Objects in Turbid Media", *Optical Society of America* 1995, pp. 629–631.

*Primary Examiner*—William E. Kamm
*Assistant Examiner*—Maulin Patel
*Attorney, Agent, or Firm*—Baker Botts L.L.P.

[57] ABSTRACT

An apparatus (10) for frequency encoded ultrasound modulated optical tomography is provided. A function generator (12) produces a frequency sweep signal which is applied to an ultrasonic transducer (20). The ultrasonic transducer (20) produces ultrasonic wave (25) in a turbid medium (21). Coherent light from a laser (22) is passed through turbid medium (21) where it is modulated by the ultrasonic wave (25). A photomultiplier tube (24) detects the light which passes through the turbid medium (21). The signal from the photomultiplier tube (24) is fed to an oscilloscope (30) and then to a computer (32) where differences in light intensity at different frequencies can determine the location of objects in the turbid medium (21).

28 Claims, 2 Drawing Sheets

METHOD AND APPARATUS FOR FREQUENCY ENCODED ULTRASOUND-MODULATED OPTICAL TOMOGRAPHY OF DENSE TURBID MEDIA

RELATED APPLICATIONS

This application claims the benefit of U.S. Provisional Application No. 60/045,918 filed May 7, 1997.

TECHNICAL FIELD OF THE INVENTION

This invention relates generally to the field of optical tomography and more particularly to a method and system for frequency encoded ultrasound-modulated optical tomography of dense turbid media.

BACKGROUND OF THE INVENTION

Breast cancer is the most common malignant neoplasm and the leading cause of cancer deaths among women in the United States. Early detection is critical to the successful treatment of this disease. Currently the most common methods of detections are mammography and ultrasound. Mammography is considered the only reliable means of detecting nonpalpable breast cancers. A drawback of mammography is that it uses ionizing radiation. Also, breast tissue can be radiologically dense, making detection difficult. Ultrasound is used primarily as either a first screening tool or as a supplement to mammography.

Other techniques for the detection of breast cancer are under investigation. Magnetic Resonance Imaging (MRI) is a technique which is superior to mammography in that it can distinguish solid lesions from cystic lesions. However, MRI is expensive, has inferior spatial resolution as compared to mammography and can not image micro calcifications. Breast cancer tomography has been investigated but is expensive, has poor spatial resolution and involves the use of intravenous injected iodinated materials.

A relatively new and active field is the use of non-ionizing laser light to detect breast cancer. The optical properties of normal and diseased breast tissue typically varies. Therefore, it is possible to detect breast cancers based on the optical differences of the tissue. This is due to the fact that cancerous tissues manifest a significant change at the cellular and sub-cellular level. For example, the scattering coefficient of fibrocystic tissue (600 cm$^{-1}$) is approximately 50 percent higher than that of normal glandular breast tissue (400 cm$^{-1}$) or 100% higher than normal breast adipose tissue (300 cm$^{-1}$) in the wavelength of 500–1000 nm.

One laser technique is called "early photon imaging." Since breast tissue is an optically turbid medium, light is quickly diffused inside tissue as a result of scattering. Light in tissue takes one of three forms: ballistic light, which travels straight through tissue without scattering; quasi-ballistic light, which experiences some scattering; and diffuse light, which is almost completely scattered inside tissue. This technique uses pulses of light and attempts to detect only the first light that is transmitted through the tissue. Because early photon imaging only detects ballistic light, this technique is mainly useful for thin tissues. Diffuse light is needed to detect thick tissues (5 cm).

In order to increase the incidence of early detection of breast cancer, it is desirable to have a system which can detect small abnormalities with good resolution at low cost and without the use of ionizing radiation.

SUMMARY OF THE INVENTION

In accordance with the present invention, a method and system for frequency encoded ultrasound-modulated optical tomography of dense turbid media is provided.

In one aspect of the present invention, an apparatus for frequency encoded ultrasound-modulated optical tomography of dense turbid medium is provided. The apparatus includes a function generator which produces a frequency sweep signal. An ultrasonic transducer receives the frequency sweep signal and converts it into an ultrasonic wave which is propagated in a turbid medium. A laser sends a coherent beam of light through the turbid medium where it is modulated by the ultrasonic wave. The modulated light is detected by a photomultiplier tube which sends the signal to an oscilloscope for determination of where an object or abnormality is located in the turbid medium.

The present invention provides various technical advantages over conventional techniques to locate objects in a turbid medium, such as cancerous tissue. For example, one technical advantage is that it uses non-ionizing radiation. Another technical advantage is that it is a low cost/cost effective system. Another technical advantage is that it has better resolution than other optical techniques. Further advantages include high acquisition speed and better optical resolution along the ultrasonic axis. Other technical advantages may be readily apparent to one skilled in the art from the following figures, descriptions and claims.

BRIEF DESCRIPTION OF THE DRAWINGS

For a more complete understanding of the present invention and for further features and advantages, reference is now made to the following description taken in conjunction with the accompanying drawings, in which.

DETAILED DESCRIPTION OF THE INVENTION

The preferred embodiment of the present invention and its advantages are best understood by referring to FIGS. 1–5 of the drawings, where like numerals are used for like and corresponding parts of the various drawings.

Figure 1:
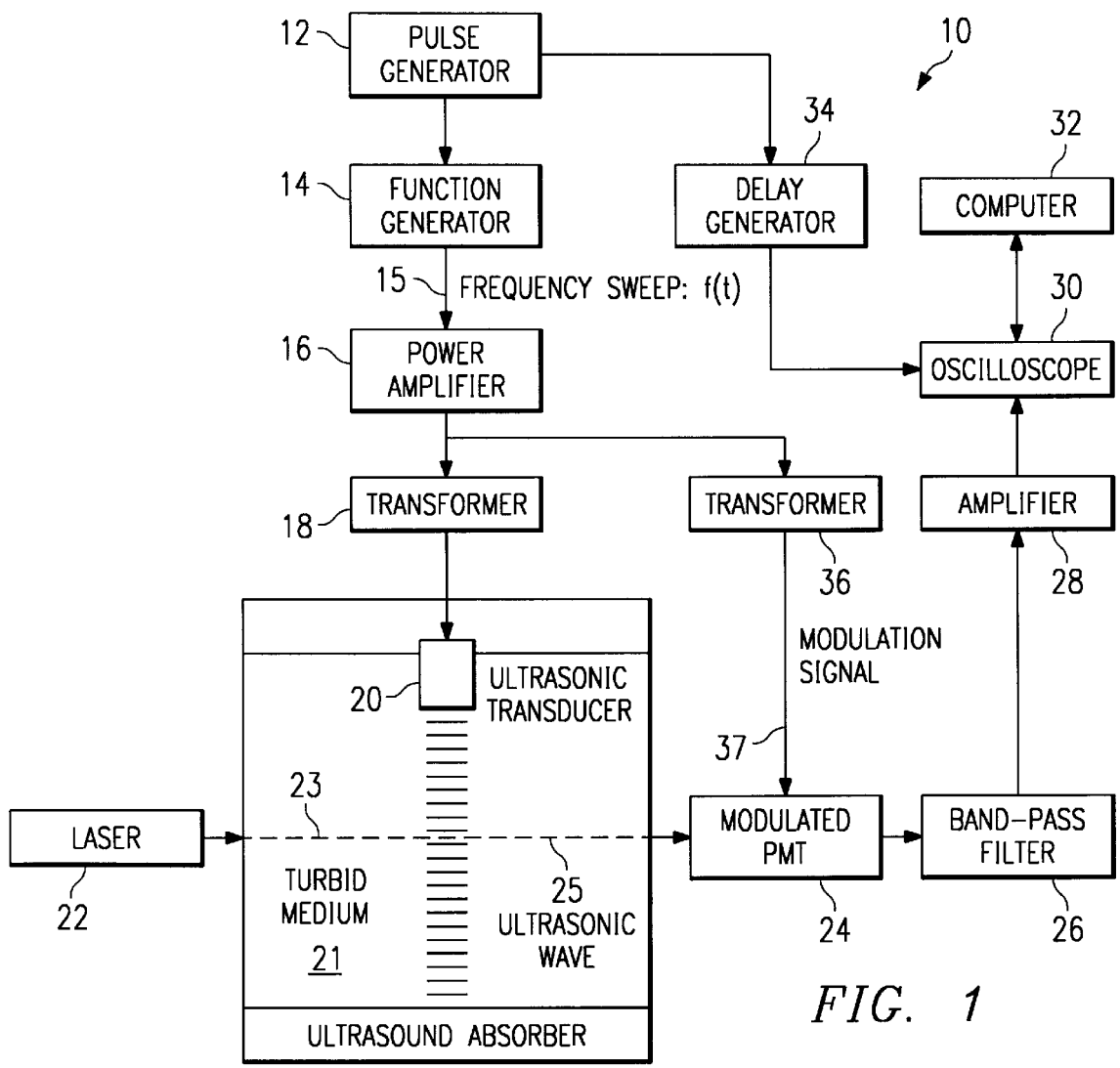
FIG. 1 illustrates a system for frequency swept ultrasonic modulated optical tomography.

FIG. 1 illustrates a system 10 for frequency encoded ultrasound-modulated optical tomography. System 10 consist of a pulse generator 12 coupled to a function generator 14 which is coupled to a power amplifier 16. Pulse generator 12 is also coupled to a delay generator 34 that couples to an oscilloscope 30. Function generator 14 couples to a power amplifier 16 and is also coupled to a transformer 36 that couples to a modulated photo-multiplier tube (PMT) 24. Power amplifier 16 is coupled to a transformer 18 that couples to an ultrasound transducer 20. The ultrasound transducer 20 is preferably in contact with a turbid medium 21 for best wave propagation. A laser 22 is located on one side of the turbid medium, roughly normal to the position of the ultrasound transducer. Laser 22 sends a coherent beam of light 23 into turbid medium 21. Modulated PMT 24 receives any light which is transmitted through turbid medium 21. Modulated PMT 24 is coupled to a band pass filter 26 which couples to an amplifier 28 and an oscilloscope 30 and finally to a computer 32.

Figure 2:
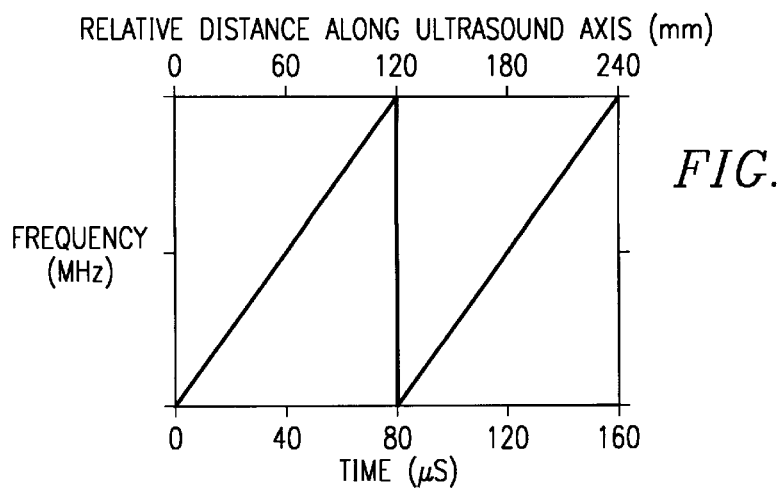
FIG. 2 illustrates a sample frequency sweep.

In operation, pulse generator 12 triggers function generator 14 to produce a frequency sweep signal 15. Frequency sweep signal 15 is a signal of linearly varying frequency that has a finite period. An example of the frequency variation in a sample frequency sweep is illustrated in FIG. 2. Frequency sweep signal 15 is amplified in power by power amplifier 16. The signal is then amplified in amplitude by transformer 18. The amplified signal is applied to ultrasound transducer 20 to generate an ultrasonic wave 25 in turbid medium 21.

Laser 22 sends a beam of coherent light 23 into the turbid medium. The diffuse light from beam of light 23 is modulated by the ultrasonic wave 25, which adds spatial information to the diffuse light. Because light travels much faster than ultrasonic wave 25, the ultrasonic-modulated optical signal reflects the instantaneous frequencies of ultrasonic wave 25.

Prior to transformer 18, the signal from power amplifier 16 is fed into transformer 36 to amplify the amplitude of the signal to form a modulation signal 37. This signal is sent to the modulated PMT 24 where it mixes with the modulated optical signal coming out of the turbid medium 21. While a PMT is illustrated in the primary embodiment, any device capable of detecting light, such as a photo diode, can be used. Band-pass filter 26 selects the signal from a zone of interest along the ultrasonic axis based on the frequency sweep rate and the time of ultrasonic propagation. The filtered signal is amplified for detection by an oscilloscope 30. Oscilloscope 30 is triggered by delay generator 34 which triggers the oscilloscope after the ultrasonic wave has had sufficient time to propagate in the turbid medium 21. Oscilloscope 30 takes and may average the results over a number of sweeps in order to increase the signal to noise ratio. Computer 32 then analyzes the signal from the oscilloscope and performs fast Fourier Transform (FFT).

The frequency spectrum will yield imaging information for the zone of interest as selected by band-pass filter 26. The frequency in the spectrum corresponds to the instantaneous frequency of the different axial positions in the zone of interest minus the instantaneous frequency of the modulation signal sent to PMT 24 and equals the frequency sweep rate times the ultrasonic propagation time from the ultrasonic transducer 20 to different positions in the zone of interest. The frequency in the spectrum can be converted into the ultrasonic propagation time from the ultrasonic transducer 20 to different positions in the zone of interest. The propagation times multiplied by the speed of the ultrasound in the medium yields the distance from the ultrasound transducer 20 to the point in the zone of interest. There is a one-to-one correspondence between the frequency in the spectrum and the position in the zone of interest. The frequency spectrum can be converted into a position spectrum, which is a one-dimensional image of the turbid medium 21 along the ultrasonic axis. Movement of the apparatus along a line perpendicular to the ultrasonic axis results in a two dimensional image while movement along a plane results in a three dimensional image.

The saw-tooth function in the frequency sweep may be replaced with a triangle function to avoid abrupt change in the instantaneous frequency. The frequency sweep may also be produced using an arbitrary wave form generator. Two function generators may also be used to deliver two frequency sweep signals. There may be a time delay and/or a frequency shift between the two frequency sweep signals.

Figure 3:
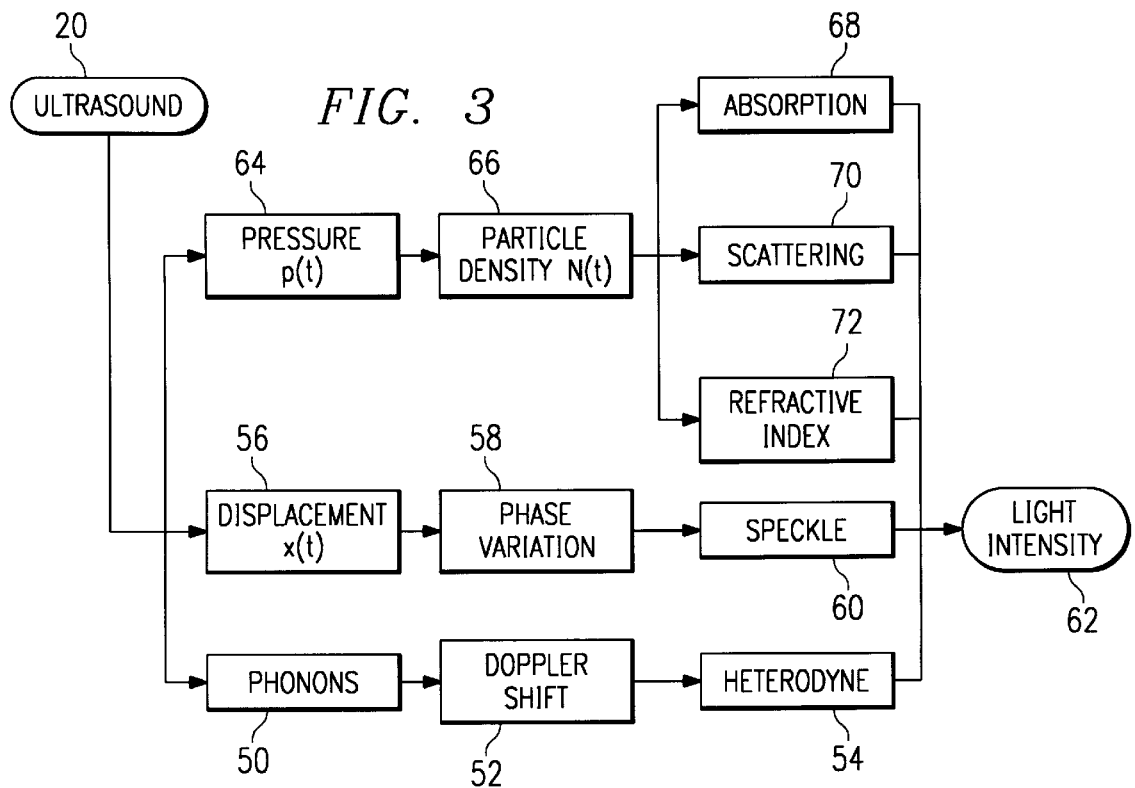
FIG. 3 illustrates a list of possible mechanisms for ultrasonic modulation of light.

FIG. 3 lists possible mechanisms for ultrasonic modulation of light. The first mechanism starts with the ultrasonic wave generating a pressure variation in the medium at step 64. This induces a density change in the medium at step 66. The optical absorption at step 78, scattering coefficient at step 70, and index of refraction at step 72 vary with density. The changes in these parameters lead to the modulated light in step 62.

Another possible mechanism is particle displacement. The ultrasonic wave generates particle displacement at step 56. This causes optical path lengths to change at step 58. Changes in optical path length leads to speckles forming in the medium at step 60, which leads to a change in light intensity at step 62.

A third mechanism is phonon-photon interaction. In step 50, the ultrasonic wave is considered to act like a phonon. The phonons interact with the photons from the laser 22 causing a Doppler shift at step 52 of the optical frequency by the ultrasonic frequency. The optical detector functions as a hetereodyning device at step 54 between the Doppler shifted light and unshifted light and produce a signal of the ultrasonic frequency.

The single ultrasonic generator 20 may be replaced by a one or two dimensional sequenced array of ultrasonic transducer elements 20. Each element is driven by a different frequency sweep signal 15 in such a way as that the frequency at any two points in time is not the same. Additionally, all or some of the ultrasonic elements 20 may be excited at the same time. If a group of elements are excited sequentially, a two dimensional image can be made from a linear ultrasonic array. A two dimensional array would yield a three dimensional image if the elements are excited sequentially. If an entire linear array is excited simultaneously, a two dimensional image along the ultrasonic axes is obtained. If a two dimensional array of elements is excited simultaneously, a three dimensional image along the ultrasonic axes is obtained.

Figure 4:
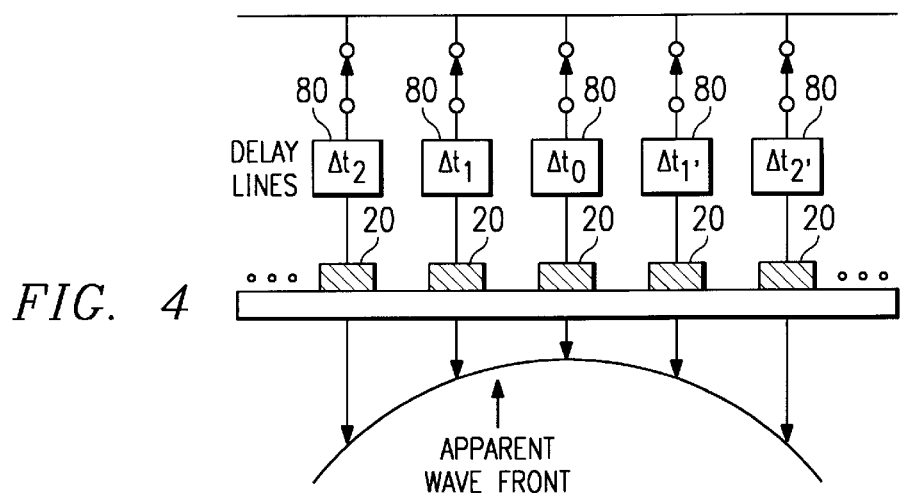
FIG. 4 illustrates an alternative embodiment of an invention using phased arrays of ultrasonic transducers.

FIG. 4 illustrates ultrasonic generation using phased arrays. In this embodiment, the single ultrasonic generator 20 is replaced by a one or two dimensional phased array ultrasonic transducer 20 elements that are connected to electronic delay lines 80. In this manner, a single frequency sweep signal 15 will be delayed and then applied to each element. By adjusting the delays, the ultrasonic focus can be adjusted. By changing the curvature of the wavefront, the depth of the focus can be adjusted. The focus can be moved horizontally by changing the symmetry of the wavefront.

Figure 5:
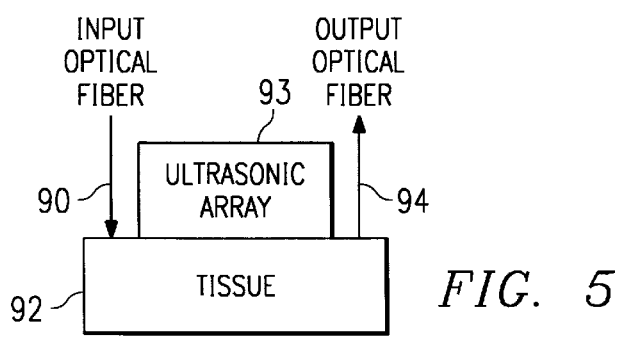
FIG. 5 illustrates a handheld embodiment of the tomography system.

FIG. 5 illustrates a handheld embodiment of the present invention. Input optical fiber 90 sends a coherent source of light into tissue 92. An ultrasonic array 93 (consisting of one or more ultrasonic generators, one or more function generators, and other electronic components) produces an ultrasonic wave in tissue 92. An output optical fiber 94 transports modulated-light for analysis.

This disclosed technique may be modified to conduct imaging using sonoluminescent light. The laser is not needed in sonoluminescence imaging. Sonoluminescent chemicals are mixed into the turbid medium. The medium is excited using ultrasound to generate ultrasound-induced light (sonoluminescent light). A similar data detection and analysis as described above would generate an image of the medium in terms of its sonoluminescent characteristics.

While the preferred embodiment has been discussed in terms of the detection of breast cancer, it is apparent from the above discussion that this apparatus can be used to detected abnormalities in other bodily locations as well as acquire images of different structures located in other turbid mediums wholly outside of the medical field such as underwater detection, atmosphere optics and other fields involving turbid mediums. It should be understood that various changes, substitutions and alterations may be readily apparent to those skilled in the art and may be made herein without departing from the spirit and scope of the invention as defined by the appended claims.

What is claimed is:

1. An apparatus for frequency encoded ultrasound modulated optical tomography comprising:
   a function generator operable to produce a frequency sweep signal;
   an ultrasonic transducer coupled to the function generator and operable to produce an ultrasonic wave in a turbid medium in response to the frequency sweep signal;
   a laser, located outside the turbid medium and operable to send a coherent beam of light into the turbid medium;
   a photo multiplier tube located outside the turbid medium and operable to detect light from the laser that has traveled through the turbid medium and that has been modulated by the ultrasonic wave; and
   an oscilloscope operable to display the output of the photo multiplier tube wherein differences in the oscilloscope display is indicative of an abnormality in the turbid medium.

2. The apparatus of claim 1, further comprising a pulse generator operable to trigger the operation of the function generator.

3. The apparatus of claim 1, further comprising a transformer operable to amplify the frequency sweep signal and to send the frequency sweep signal to the oscilloscope as a modulation signal.

4. The apparatus of claim 1, further comprising a computer coupled to the oscilloscope and operable to receive data from the oscilloscope and to process the data to enable determination of different structures in the turbid medium.

5. The apparatus of claim 1, wherein the ultrasonic transducer comprises a plurality of individual ultrasonic transducer elements coupled to individual function generators.

6. The apparatus of claim 5, wherein a portion of the plurality of individual ultrasonic transducer elements are operated sequentially.

7. The apparatus of claim 5, further comprising a time delay means coupled to each of the plurality of individual ultrasonic transducer elements and operable to delay the frequency sweep signal from the function generator to the plurality of individual ultrasonic generator.

8. The apparatus of claim 1, further comprising a band pass filter operable to select frequencies of interest.

9. The apparatus of claim 1, wherein the turbid medium is human tissue.

10. The apparatus of claim 1, wherein the abnormality is a neoplasm.

11. A method for imaging an object located in a turbid medium comprising the steps of:
   producing a frequency sweep signal;
   producing an ultrasonic wave in the turbid medium in response to the frequency sweep signal;
   sending a coherent beam of light into the turbid medium;
   receiving a portion of the coherent beam of light that has been modulated by the ultrasonic wave and that has passed through the turbid medium, the coherent beam of light modulated by the ultrasound wave indicating a location of an object in the turbid medium;
   determining the location of the object located in the turbid medium from the coherent beam of light.

12. The method of claim 11, wherein the turbid medium is human tissue.

13. The method of claim 11, wherein the object located in the turbid medium is a neoplasm.

14. The method of claim 11, wherein the step of producing an ultrasonic wave further comprises the step of sequential operating a portion of an array of ultrasound generators.

15. The method of claim 11, wherein the step of producing an ultrasonic wave further comprises the step of using a time delay circuit to operate a phased array of ultrasound generators.

16. The method of claim 11, wherein the step of producing a frequency sweep signal further comprises the step of triggering the function generator with a pulse generator.

17. The method of claim 11, further comprising the step of mixing a modulated signal from the function generator with the portion of the coherent light that traveled through the turbid medium.

18. The method of claim 11, further comprising the step of selecting frequencies of interest with a band pass filter.

19. An apparatus for the detection of objects located in a turbid medium comprising:
   a function generator operable to produce a frequency sweep signal;
   an ultrasonic transducer coupled to the function generator and a turbid medium and operable to produce an ultrasonic wave in the turbid medium in response to the frequency sweep signal;
   a light source, located outside the turbid medium and operable to send a coherent beam of light into the turbid medium;
   a light detection device located outside the turbid medium and operable to detect light from the light source that has traveled through the turbid medium and that has been modulated by the ultrasonic wave; and
   a computer operable to translate the signal from the light detection device and determine the location of an object in the turbid medium.

20. The apparatus of claim 19, further comprising a pulse generator operable to trigger the operation of the function generator.

21. The apparatus of claim 19, further comprising a transformer operable to amplify the frequency sweep signal and to send the frequency sweep signal to the light detection device as a modulation signal.

22. The apparatus of claim 19, wherein the ultrasonic transducer comprises a plurality of individual ultrasonic transducer elements coupled to individual function generators.

23. The apparatus of claim 22, wherein a portion of the plurality of individual ultrasonic transducer elements are operated sequentially.

24. The apparatus of claim 22, further comprising a time delay means coupled to each of the plurality of individual ultrasonic transducer elements and operable to delay the frequency sweep signal from the function generator to the plurality of individual ultrasonic transducer elements.

25. The apparatus of claim 19, further comprising a band pass filter operable to select frequencies of interest.

26. The apparatus of claim 19, wherein the turbid medium is human tissue.

27. The apparatus of claim 19, wherein the object is a neoplasm.

28. The apparatus of claim 19, wherein the light source is a laser.

* * * * *